United States Patent [19]

Laméris et al.

[11] 3,941,658
[45] Mar. 2, 1976

[54] METHOD FOR DETERMINATION OF THE PRESENCE OF ANTIBIOTICS

[75] Inventors: Sophia Adriana Laméris, Hague; Jan Lambert van Os, Voorburg; Joannes Gerard Oostendorp, Rijswijk-Zh, all of Netherlands

[73] Assignee: Gist-Brocades N.V., Delft, Netherlands

[22] Filed: May 22, 1974

[21] Appl. No.: 472,511

[30] Foreign Application Priority Data
May 31, 1973 United Kingdom............... 25947/73

[52] U.S. Cl........................................... 195/103.5 R
[51] Int. Cl.² ......................................... C12K 1/04
[58] Field of Search....... 195/103.5 R, 99, 100, 101, 195/102

[56] References Cited
UNITED STATES PATENTS

| | | | |
|---|---|---|---|
| 2,967,132 | 1/1961 | Sacks............................ | 195/103.5 R |
| 3,063,916 | 11/1962 | Kosikowski................... | 195/103.5 R |
| 3,126,325 | 3/1964 | Poole............................ | 195/103.5 R |

OTHER PUBLICATIONS

H. Mol, "A Rapid and Sensitive Test for the Detection of Penicillin in Milk, Using Test Plates Which Can Be Kept in Stock Ready for Use," Neth. Milk Dairy J. 23 (1969) pp. 153–163.

*Primary Examiner*—A. Louis Monacell
*Assistant Examiner*—C. A. Fan
*Attorney, Agent, or Firm*—Hammond & Littell

[57] ABSTRACT

A method for the rapid determination of the presence or absence of residues of antibiotic such as penicillin, in liquids, for example milk, and meat comprising introducing spores of a microorganism which possesses a high sensitivity for the antibiotic to be determined into an agar medium so that the spores are prevented from starting to germ due to lack of nutrients, but stay alive, and being sufficiently heavily inoculated that after addition of nutrients and incubation at or near optimal temperature in a short time sufficient growth has proceeded so that growth is either observable visually or its indicated by an indicator added to the agar medium, the said spore culture being allowed to solidify in upright test vessels having a cross-sectional dimension sufficiently small to require as little of the agar medium as possible but sufficiently large to enable a correct determination of inhibition of growth of the microorganism to be made, and having a height so that the vessel can contain a sufficient amount of medium and a sufficient amount of sample of liquid to be tested, placing on the agar surface nutrients required for growth, followed, if desired, after a pre-incubation period, by addition of a predetermined amount of sample liquid to be tested to the test vessel, and incubating the contents of the test vessel at or near optimal temperature for a predetermined time so that the extent of growth or inhibition of growth of the microorganism read in a vertical sense, indicates absence or presence of the antibiotic.

27 Claims, No Drawings

METHOD FOR DETERMINATION OF THE PRESENCE OF ANTIBIOTICS

STATE OF THE ART

Methods for the determination of antibiotic residues, particularly penicillin residues, in milk and similar liquids have been known for a long time, and several standard methods are accepted officially for the purpose in some countries. Examples thereof are the so-called TTC-method involving 2,3, 5-triphenyl-tetrazolium chloride such as the method of Neal et al [J. Dairy Science, Vol. 38 (1955), p. 629–633] and a method using *Bacillus stearothermophilus* or *B. calidolactis* of Galesloot et al. [Neth. Milk & Dairy J. Vol. 16 (1962), p. 89–95] based on a method of Vincent et al. [Proc. Soc. exp. Biol. Med. Vol. 162 (1944), p. 55] and the method of Jacobs et al. [Tijdschr. v. Diergeneesk Vol. 79 (1972):9, p. 548–550]. The method of Galesloot et al is carried out by placing paper discs soaked in the milk to be tested on agar cultures of *Bacillus stearothermophilus* or *B. calidolactis* on petri dishes and incubating at 55°C for 2½ hous. Formation of inhibition zones is an indication of the presence of penicillin or other substances inhibiting these bacilli in the milk.

The method of Galesbot et al. has a sensitivity of about 0.0025 IU (international units) of penicillin per ml, but this method is not suitable to be carried out by unskilled persons because of the necessity to use fresh cultures of the bacilli. Furthermore, the reliability of this test is relatively low when carried out by less skilled persons.

To increase the reliability of the Galesloot method, H. Mol. [Neth. Milk & Dairy. J. Vol. 23 (1969), p. 153–162] made use of spores of *Bacillus stearothermophilus* var. *calidolactis* prepared in petri dishes. Before use, a nutrient disc obtained by soaking a piece of filter paper in an aqueous solution of 20% of peptone and 20% of glucose followed by drying is soaked in the sample of milk and placed on the agar. The petri dish is incubated for 6 hours at 63°C, and the presence of penicillin is recognized by the presence of an inhibition zone.

Although reliability is increased, in the method of Mol the method still has several disadvantages. In the first place, it is difficult to recognize the inhibition zone, especially for unskilled persons. Furthermore, the volume of sample is insufficiently reproducible.

For a suitable rapid test, the following requirements should be fulfilled:

i. it should be rapid,
ii. it should show a high sensitivity for a wide range of antibiotics used in practice,
iii. the vessels containing test material should be storable for a reasonably long time (several months or longer),
iv. the test should be cheap and
v. the test should give reliable results even when carried out by unskilled people, e.g. when the test is adapted to show the presence of a predetermined concentration of antibiotic, it should give sufficiently reliable positive or negative results.

Although the method of Mol fulfills requirements (i) to (iv) to a certain extent, requirement (v) is not fulfilled and qualified people are needed to carry out the method to obtain reliable results.

OBJECTS OF THE INVENTION

It is an object of the invention to provide a rapid, simple method for the determination of the possible presence of antibiotic in liquids fulfilling all the above requirements, particularly by unskilled personnel.

It is another object of the invention to provide a novel test apparatus which can be used to rapidly determine the possible presence of antibiotic in liquids.

These and other objects and advantages of the invention will become obvious from the following detailed description.

THE INVENTION

The novel process of the invention for the rapid determination of the presence or absence of residues of antibiotic, for example penicillin, in liquids such as milk and meat comprises introducing spores of a microorganism which possesses a high sensitivity for the antibiotic to be determined in an agar medium so that the spores are prevented from starting to germ due to lack of nutrients but stay alive, and being sufficiently heavily inoculated that after addition of nutrients and incubation at or near optimal temperature in a short time sufficient growth has proceeded so that growth is either observable visually or is indicated by an indicator added to the agar medium, the said spore culture being allowed to solidify in upright test vessels having a cross-sectional dimension sufficiently small to require as little of the agar medium as possible, but sufficiently large to enable a correct determination of inhibition of growth of the microorganism to be made, preferably 3–20 mm, more preferably 6–14 mm, and having a height so that the vessel can contain a sufficient amount of medium (determined by the test time and diffusion speed of the nutrients) and a sufficient amount of sample of liquid to be tested, the height of medium and sample together preferably being 3–30 mm, more preferably 5–10 mm, placing on the agar surface nutrients required for growth, followed, if desired after a pre-incubation period, by addition of a predetermined amount of sample liquid to be tested (different amounts of sample influence the results of the test) to the test vessel, and incubating the contents of the test vessel at or near optimal temperatures for a predetermined time so that the extent of growth or inhibition of growth of the microorganism read in a vertical sense indicates absence or presence of antibiotic.

When the method is standardized, the test can be carried out easily with reliable results, even by unskilled persons, and in some cases, even a rough quantitative estimate of the amount of antibiotic present in the sample can be made, or the presence of a concentration exceeding the sensitivity may be detected. The solidification of the agar medium in upright position of the test vessel, combined with standardized amounts of sample and medium, has the advantage that the size of the surface area of the agar medium is well defined so that when introducing the nutrient compounds, reliable incubation results are obtained which may be semi-quantitative.

An indicator may be added to the agar medium containing the spores or to the nutrients. If ann indicator is included in the agar medium, a bettr distribution in the medium is obtained before the test is carried out. Furthermore, the sensitivity of the test is higher, and for liquids other than milk, the color is less contaminated by color impurities originating from the sample. The indicator may be an acid base indicator such as bromocresol purple or phenol red, or a redox indicator such as 2,3,5-triphenyl-tetrazolium chloride. For the determination of penicillin, the use of bromocresol purple is preferred.

The pH of the medium is important as well for the optimal growth rate of the test organism as for the activity of the antibiotics to be tested, and thus for the sensitivity of the microorganism to the antibiotics. For *Bacillus stearothermophilus* var. *calidoactis*, for example, the pH of the medium should be about 7 in the beginning of the test period to obtain an optimal growth rate. By using a suitable indicator such as bromocresol purple, a very short test period may be achieved.

Although the test period will be somewhat longer, the sensitivity of the test to certain antibiotics, especially aminoglucoside antibiotics such as streptomycin, dihydrostreptomycin, kanamycin and neomycin, may be increased by starting the test with a medium having a pH of about 8. A suitable indicator in this case is phenol red, for example. The sensitivity to the other antibiotics, however, is not influenced disadvantageously, when the pH of the medium during the test decreases so that each antibiotic at its suitable pH inhibits the growth of the microorganism. The pH range between the start and the finish of the test may be extended by using mixed indicators, if desired.

The sensitivity of the test to certain antibiotics may be adapted by using more suitable spores or combinations of spores.

For the purpose of the invention, spores may be used from all bacteria which can form spores and are sufficiently sensitive to the antibiotic(s) to be tested. A suitable spectrum of sensitivities to different antibiotics may be obtained by using spores of one species or strain, or by using a mixture of spores of different organisms. Suitable spores are those of spore producers of the genus Bacillus with suitable sensitivity to the antibiotics involved such as *Bacillus calidolactis* [Hussong et al., J. Bact., Vol. 15 (1928), p. 179–188], *Bacillus subtilis*, *Bacillus stearothermophilus* [Bergey's Manual of Determinative Bacteriology, 7th Ed., (1957) p. 613–693], the thermophilic bacilli described by Galesloot et al. [Neth. Milk & Dairy J. Vol. 13 (1959), p. 155–179], *Bacillus stearothermophilus* var. *calidolactis* [Mol, Neth. Milk & Dairy J. Vol. 23 (1969), p. 153–162] and *Bacillus calidolactis* strain C 953 of the Netherlands Institute for Dairy Research at Ede, The Netherlands [Galesloot et al., Neth. Milk & Dairy J. Vol. 16 (1962), p. 89–95].

Preferably, spores are used of *Bacillus stearothermophilis* var. *calidolactis*, which is deposited with the Laboratory for Microbiology at Delft, The Netherlands, and assigned the number L.M.D. 74.1. This microorganism has a high sensitivity to penicillin G and pencillin V and a very high growth rate, and has the additional advantage that its optimal growth temperature is relatively high whereas other microorganisms normally don't grow whereby the chance of infection is reduced. Spores of this microorganism are not only sensitive to penicillin G and penicillin V and other natural penicillins, but are also sensitive to several other antibiotics, such as semi-synthetic penicillins, e.g. nafcillin and cloxacillin; cephalosporins; aminoglucoside antibiotics, e.g. streptomycin, dihydrostreptomycin, neomycin and kanamycin; tetracyclines, e.g. chlorotetracycline; chloramphenicol; macrolide antibiotics, e.g. oleandomycin and erythromycin; polypeptide antibiotics; and several chemotherapeutics, e.g. trimetroprim, sulfadoxine and furazolidone, so that the method according to the invention is also useful to indicate the presence of these antibiotics and chemotherapeutics, if necessary, after adaption of the pH.

For use in accordance with the invention, the culture preferably contains $10^5$ to $10^8$ spores of microorganism per ml of agar medium, more particularly $10^6$ to $10^7$ spores per ml of medium. A suitable manner of preparing the spore culture is cultivation of the microorganism in surface culture on agar or in a submerged liquid culture, e.g. in shaken flasks or in a fermenter as described by Yao et al. [Appl. Microbiol. Vol. 15 (1967), p. 455]. The spores are preferably incorporated into the agar medium in a manner such that the spores stay alive but are prevented from germination. Physiological salt solutions and/or an indicator may be added to the agar, but it should not contain nutrients for the microorganism.

It is an additional advantage of the method of the invention that the influence of inhibitors, e.g. products produced by leucocytes which are normally present in milk and other liquids to be tested and which are not antibiotics, is decreased to a considerable extent which is normally not the case in previously known methods. The decrease of influence of these inhibitors is due to the fact that they do not, or do not to a substantial extent, diffuse into the agar inside the test vessels, e.g. test tubes. It is evident that this fact increases the reliability of the method of the invention, which has the further advantage of being a handy test since pre-treatment of the milk to inactivate those inhibitors is normally not necessary, even when samples of milk with a slightly altered appearance are presented.

The agar medium containing the spores is allowed to solidify in upright test vessels. Those vessels preferably have predetermined sizes so that the test results are sufficiently reliable. The test of the invention is even quantitative to some extent as, when the test is carried out under certain predetermined circumstances, the antibiotic diffuses into the agar forming a gradient of decreasing concentrations in the agar. In the region where the concentration of the antibiotic is below a certain level, inhibition of growth will not occur so that the medium is influenced by the growth of the microorganism, and the indicator when present changes its color. The region where the concentration of the antibiotic is above this level, inhibition of growth occurs and the indicator will not change its color. The height of the agar medium in the test vessel, e.g. test tube, where the color of the indicator changes, defines the sensitivity of the test. The sensitivity may be ascertained in the vessels of the invention by standardizing the height of the solidified agar in the vessel. This feature may be used advantageously to develop a test in which the height of the spore-containing agar is selected in such a manner that the indicator changes its color when the antibiotic is present in a concentration below a certain value, but does not change its color when the concentration of the antibiotic is above this value.

The cross-sectional dimension of the test vessels is preferably 3–20 mm, more preferably 6–14 mm, and the height is such that the vessels may contain an amount of medium and sample corresponding to a height of preferably 3–30 mm. When the test is arranged to be a quantitative test, i.e. a test in which some quantitative results may be read from the height of the inhibition zone, this height is preferably 20–30 mm. When the test is arranged to be a test from which one can read whether a certain concentration of antibiotic is present or not, the height is preferably 5–15 mm.

When filled with a predetermined amount of the liquid agar medium, the contents are allowed to solidify when the test vessels are in upright position so that a horizontal agar surface is obtained. The test vessels containing the solidified agar medium containing the spores may be closed in which condition they may be stored for at least several months, if necessary in a refrigerator, without the spores losing their viability.

When carrying out the test for the presence of an antibiotic, the required nutrient compounds which may contain an indicator are first placed on the surface of the spore-containing agar medium in the test vessel. Although a predetermined amount of the nutrient compounds in liquid form may be placed on the surface of the agar medium, it is preferred to use the nutrients in dry form, preferably in the form of filter paper discs or tablets containing the required nutrient compounds in a dried state so that the nutrients have a better storage stability. The discs or tablets should be smaller than the cross-sectional area of the vessel to prevent air entrapment when the disc or tablet is laid on the medium as air entrapment would influence the diffusion pattern in the agar. Nutrients to be used should contain at least an assimilable carbon source and nitrogen source, preferably in the form of glucose and peptone, depending on the strain applied. The nutrient discs or tablets may contain the indicator and/or buffer.

After placing the nutrient compounds on the surface of the agar medium, a predetermined amount of the liquid to be tested, generally milk, or meat, is added to the contents of the test vessel. This may be done directly after placing the nutrients on the surface of the agar medium or after a pre-incubation period. When the nutrients are in a dry form, in the pre-incubation method, some water or physiological salt solution may also be added. The latter procedure has the advantage that, for example, when a batch of milk arrives in a factory where it is used for certain purposes, e.g. for distribution as milk for human consumption, for butter and cheese making or for yogurt fermentation which may only be done after the absence of penicillin (or other antibiotic) residues has been established, the period during which the batch should wait before being further used until the results of the test are known may be shorter. By applying a pre-incubation period, the incubation in the presence of the sample to be tested may be shorter than when a pre-incubation period is not applied. The pre-incubation period may be, depending on the circumstances, up to about 1 hour.

It is also possible to make a more economical use of the time during which the liquid to be tested, generally milk, is transported to the factory by starting the test during the transport using thermoblocs to keep the temperature constant. Also, a combination of the above-indicated measures may be applied.

The incubation period (including the pre-incubation period) is dependent on the circumstances, e.g. the spores used and the nutrient and temperatures applied. When using spores of Bacillus stearothermophilus var. calidolactis, suitable incubation temperatures are about 55° to 70°C, preferably 60° to 65°C and incubation periods within which reliable results may be obtained are relatively short and vary from about 1½ to 4 hours, preferably from 2 to 3 hours.

Although the test has been developed especially for application of milk, the test may also be used for other materials such as meat. For example, a small piece of meat placed directly on the agar, or meat liquid squeezed from a sample of meat, or drip liquid from deep-frozen and defrosted meat. For that purpose, the nutrients must be adapted to neutralize disturbing factors. This may be done by the addition of suitable chemicals, e.g. pH buffers, to the test. Disturbing factors such as lactoferine and seroferine may be neutralized by the addition of ferrous sulfate.

As a pre-screening for the residues of antibiotics in slaughter animals, the test can be applied to urine since antibiotics accumulate therein. For testing undiluted urine, the pH should be adapted to the test by use of suitable pH buffers in the tablet. Urine samples may also be tested without using additives. In this case, it is necessary, however, to dilute the samples about 10 times with water.

To determine whether an antibiotic present in a sample is a penicillin or another antibiotic, it is possible to carry out the test with two test vessels. To one of the vessels, a nutrient tablet or an additional tablet or disc is added containing penicillinase, while to the other vessel, a nutrient tablet is added without penicillinase addition. When penicillinase is present, the non-penicillinase-resistant penicillins will be decomposed during the test. One could also use another specific penicillin inactivator instead of penicillinase such as cysteine.

According to another feature, the invention provides a test vessel for the rapid determination of residues of antibiotic, for example penicillin, in liquids, for example milk, or meat, comprising spores of a microorganism which possesses a high sensitivity to the antibiotic to be tested in an agar medium being sufficiently heavily inoculated that after addition of nutrients and incubation at or near optimal temperature in a short time sufficient growth has proceeded that either growth is observable visually or is indicated by an indicator added to the medium, the said spore culture being solidified in the test vessel in its upright position. The test vessel may have the dimensions in width and height heretofore particularly mentioned.

It will be appreciated that combinations of a certain number of test vessels, e.g. a block of translucent material provided with a number of holes shaped to form test vessels of the invention, are also within the scope of the present invention. In another embodiment, the vessels which may be in the form of test tubes or ampoules containing the spore suspension may be combined into a set by means of a suitable rack or basket.

As mentioned above, the test vessels containing the agar medium may be stored for a prolonged period depending on maintenance of suitable storage conditions, especially temperatures.

The pH of the agar medium in the test vessel is affected during storage, by the ambient air, probably due to the presence of carbon dioxide in the air. Therefore, the test vessels such as ampoules are preferably closed air-tight during storage.

Sometimes, the agar tends to come loose from the wall of the vessel. This tendency may be decreased by adding to the agar a sticking agent which should not act as a nutrient or an inhibitor for the spores. Examples of suitable sticking agents are sodium carboxymethylcellulose and sorbitan esters known as Tween.

According to still another feature, the invention provides a test set for the rapid determination of residues of antibiotic, for example penicillin, in liquids, for example milk or meat, comprising one or more test vessels as indicated above and a corresponding amount of discs or tablets containing the required nutrients in dried form as indicated above, and optionally instruments for placing a disc or tablet on the surface of the agar medium and bringing a predetermined amount of sample liquid onto the agar surface. Such a set may be wrapped in a suitable packaging material such as styropore (a foamed polystyrene) plastic material.

The test vessels according to the invention may also contain included the nutrient discs or tablets. Since the discs or tablets withdraw moisture from the agar medium, they are coated for that purpose with a layer avoiding moisture transport from the medium into the tablets or discs at ordinary or storage temperatures, but allowing nutrients transport under the test conditions. An example of a suitable coating is a coating of wax having a melting temperature of about 35° to 55°C preferably 40° to 45°C.

The set may also contain other useful attributes, for example, a check picture from which a rough estimation of the penicillin or other antibiotic content may be read from the height of the inhibition zone. It may further contain a device for introducing a predetermined amount of sample into the test vessel. Preferably, one blank sample without penicillin or other antibiotic, e.g. plain water, may be included to control the good working of the set.

As indicated above the method of the invention may be used for determination of antibiotic residues, for example penicillin residues, in milk. However, residues of antibiotics in other liquids may also be determined by means of the method of the invention, for example, residues in the liquid which is obtained by squeezing meat, organs, kidneys, drip liquid, food-and feed-stuffs, and other liquids such as blood serum and urine. If necessary, buffers may be added to control the pH. The buffers may be different depending on the animal.

It will be appreciated that other microorganisms may be used to detect other antibiotics if used in practice. This, of course, may involve adaption of the medium, the nutrients and the incubation conditions.

In the following examples there are described several preferred embodiments to illustrate the invention. However, it should be understood that the invention is not intended to be limited to the specific embodiment.

EXAMPLE I

Preparation of test tubes

A culture of *Bacillus stearothermophilus* var. *calidolactis* L.M.D. 74.1 was inoculated on a medium consisting of:

| | | |
|---|---|---|
| Bacto nutrient agar, Difco code 0001 | 15 | g |
| Bacto agar, Difco code 0140 | 5 | g |
| dextrose | 0.5 | g |
| MnSO$_4$.H$_2$O | 30 | mg |
| distilled water to | 1000 | ml |
| sterilized for 20 minutes at 120°C. | | |

After inoculation, the medium was incubated at 60°C for at least 48 hours until a good sporulation was observed. The spores were then collected, washed with distilled water and stored at 4°C. The amount of viable spores was detected by testing on a medium consisting of:

| | | |
|---|---|---|
| Bacto agar, Difco code 0140 | 20 | g |
| Bacto Tryptone, Difco code 0123 | 8.5 | g |
| Phytone Pepton, BBL code 11905 | 1.5 | g |
| dextrose | 5 | g |
| distilled water to | 1000 | ml |
| sterilized for 20 minutes at 120°C. | | |

After inoculation, the medium was incubated for 48 hours at 60°C after which the colonies were counted. Distilled water was added to, or water was removed from, the spore suspension until the suspension contained about $10^8$ viable germs per ml. One percent of the above-mentioned spore suspension containing $10^8$ germs per ml was added to the following solution:

| | | |
|---|---|---|
| Bacto agar, Difco code 0140 | 12 | g |
| sodium chloride | 9 | g |
| distilled water to | 1000 | ml |
| sterilized for 20 minutes at 120°C. | | |

The medium was liquified by heating and then was cooled at 60°C. Sterile test tubes having cross-sectional dimensions of about 9 mm were each filled with 0.5 ml of the thus obtained medium and the contents of the test tubes were allowed to solidify with the tubes being held in an upright position. The tubes were stored at a temperature of 4°C.

Preparation of nutrient discs

The following media were prepared:

| | | | |
|---|---|---|---|
| (a) | Bromocresol purple (0.1 g) dissolved in 9.2 ml of 0.02 N NaOH was diluted with distilled water to make 25 ml. | | |
| (b) | dextrose | 50 | g |
| | distilled water | 50 | ml |
| (c) | Bacto Tryptone, Difco code 0123 | 34 | g |
| | Phytone Pepton, BBL code 11905 | 6 | g |
| | distilled water | 100 | ml |

Solutions (a) and (b) were sterilized by passage through a Seitz filter and medium (c) was sterilized at 110°C for 30 minutes and medium (c) remained a suspension. Five parts of solution (a), two parts of solution (b) and three parts of suspension (c) were mixed together, and 0.04 ml of the solution obtained was contacted with filter paper discs having a cross-sectional dimension of about 8 mm, and the discs were then dried

EXAMPLE II

Carrying out a test

Amounts of penicillin G were added to fresh cow's milk in concentrations of 0.1, 0.03, 0.01, 0.003 and 0.001 IU per ml, while one sample of cow's milk without penicillin G was run as a blank test. Six test tubes, prepared by the method of Example I, were each provided with a nutrient disc and 0.2 ml of each of the samples were added to the test tubes. Immediately, the test tubes were placed in a water bath of 65°C and observations were made after 3 and 4 hours. The results were:

Blank sample: the agar turned yellow. In the samples with less than 0.01 IU per ml; the agar was colored yellow and In the samples with 0.01 IU per ml and higher; the medium was colored violet.

EXAMPLE III

Sensitivity of the test compared with sensitivities of known tests

In the following table, the sensitivity of the test of Example I was compared with sensitivities of known tests for the determination of residues of antibiotics: a kidney test used in The Netherlands described by Schothorst and Peelen-Knol in Tijdschr. v. Diergeneesk; Vol. 95 (1970), p. 438–445; and a German method developed by the German Bundesgesundheits-Amt. cf. Levetzow, Bundesgesundheitsblatt Vol. 14(1971) p. 30–42 and Bartels et al., Die Fleischwirtschaft Vol. 52(1972) p. 479–482. The test of the invention was carried out in two ways: in the first place, the test was carried out with the antibiotics indicated below dissolved in saline, and in the second place, with milk contaminated with the indicated antibiotics. The first test gives an impression as to what may be expected when the test is carried out as a meat test.

It is clear from the table, in which the sensitivities are indicated in μg/ml, that the test of the invention is more sensitive than the kidney test for most of the antibiotics tested. This is also true for the comparison with the German test where it may be appreciated that the test of the invention is much more sensitive to penicillin.

TABLE

| | Antibiotic | Test of Invention | | Kidney test S. lutea 40 ml per plate | Modifications kidney test; S. lutea 20 ml per plate | | German method B.subtilis | |
| | | Upper limit in phys. salt sol. | Under and upper limit in milk | | pH 6 | pH 8 | pH 6 | pH 8 |
|---|---|---|---|---|---|---|---|---|
| 1 | penicillin Na-salt | 0.004 | 0.003–0.005 | 0.04 | 0.02 | 0.02 | 0.01 | 0.01 |
| 2 | kanamycin | 10 | 20–30 | ca.200 | ca.200 | 16 | 3 | 0.9 |
| 3 | neomycin | 2 | 2–8 | ca.600 | ca.400 | 1 | 10 | 0.1 |
| 4 | streptomycin | 10 | 18–22 | 80–100 | 40 | 1 | 1 | 0.2 |
| 5 | crythromycin | 0.8 | 1.5–3 | 1–2 | 0.8–1 | 0.05 | 20 | 0.8 |
| 6 | oleandomycin | 5 | 5–10 | 8–10 | 7 | 0.05 | 20 | 0.2 |
| 7 | spiramycin | | > 10 | ca.150 | ca.100 | 0.4 | > 200 | 2 |
| 8 | oxytetracyclin | 0.1 | 0.2–0.5 | 2–4 | 2 | ca.10 | 0.5 | 8 (?) |
| 9 | chlorotetracyclin | | 0.15–0.4 | ca.0.8 | 0.6 | 1 | 0.08 | 0.4 |
| 10 | tetracyclin-HCl | 0.05 | 0.15–0.4 | 2–4 | 2 | > 10 | 0.5 | 8 |
| 11 | rifamycin | | 0.03–0.04 | 0.03 | 0.01 | 0.02 | 0.02 | 0.04 |
| 12 | zinc bacitracin | 0.1 | 0.2–0.4 | 1 | 0.6 | 4 | ca.300 | ca.500 |
| 13 | chloramphenicol | 8 | 5–7.5 | 5–8 | 4 | 6 | 5 | 8 |
| 14 | nafcillin | 0.04 | 0,01–0.02 | 0.2 | 0.1 | 0.1 | 4 | > 10 |
| 15 | furazolidone | 5 | ?–8 | ca.100 | ca.60 | > 100 | 1 | 2 |
| 16 | sulfamezathin | | > 1000 | ca.2000 | ca.1000 | ca.700 | ca.700 | ca.200 |
| 17 | 1) | | 0.6–0.8 | 50 S;12 T | 20 S;4T | 8 S; 1.2 T | 5 S; 1 T | 4 S; 0.8 T |
| 18 | spectinomycin | 4 | 1–? | ca.1000 | ca.600 | 30 | 70 | 30 |
| 19 | lincomycin | 0.6 | ?–0.5 | ca.2 | 1 | 0.1 | 500 | 5 |
| 20 | cloxacillin | | 0.003–0.004 | 0.4 | 0.2 | 0.4 | 0.2 | 0.4 |

1) 200 mg sulfadoxin + 40 mg trimetroprim

Various modifications of the tests and the method of the invention may be made without departing from the spirit or scope thereof and it is to be understood that the invention is to be limited only as defined in the appended claims.

We claim:

1. A method for the rapid determination of the presence or absence of residues of antibiotic in liquids and meat comprising introducing spores of a microorganism which possesses a high sensitivity for the antibiotic to be determined in an agar medium so that the spores are prevented from starting to germ by lack of nutrients, but stay alive, and being sufficiently heavily inoculated that after addition of nutrients and incubation at or near optimal temperature in a short time sufficient growth has proceeded that growth is indicated by an indicator added either to the agar medium or to the nutrients, the resulting spore and agar mixture being allowed to solidify in upright test vessels having a cross-sectional dimension sufficiently small to require as little of the agar medium as possible, but sufficiently large to enable a correct determination of inhibition of growth of the microorganism to be made and having a height so that the vessel can contain a sufficient amount of medium and a sufficient amount of sample liquid to be tested, placing on the agar surface dried nutrients, in the form of a filter paper disc or tablet, required for growth, adding a predetermined amount of sample liquid to be tested to the test vessel, and incubating at or near optimal temperature the contents of the test vessel for a predetermined time so that the extent of growth or inhibition of growth of the microorganism read in a vertical sense indicates absence or presence of antibiotic.

2. The method of claim 1 wherein the cross-sectional dimension of the test vessels is 3 to 20 mm.

3. The method of claim 2 wherein the cross-sectional dimension of the test vessels is .6 to 14 mm.

4. The method of claim 1 wherein the height of the sample to be tested and the medium is 3 to 30 mm.

5. The method of claim 4 wherein the height of the sample to be tested and the medium is 5 to 10 mm.

6. The method of claim 1 wherein preincubation is effected before addition of the sample liquid.

7. The method of claim 1 wherein an indicator is added to the spore culture in the agar medium.

8. The method of claim 1 wherein an indicator is added to the nutrients.

9. The method of claim 7 wherein the indicator is an acid base indicator.

10. The method of claim 9 wherein the indicator is selected from the group consisting of bromocresol purple and phenol red.

11. The method of claim 7 wherein the indicator is a redox indicator.

12. The method of claim 11 wherein the redox indicator is 2,3,5-triphenyl-tetrazolium chloride.

13. The method of claim 1 wherein the pH of the medium is about 7 at the beginning of the test period to obtain an optimal growth rate.

14. The method of claim 1 wherein the pH of the medium is about 8 at the beginning of the test period to adapt the sensitivity of the test to aminoglucoside antibiotics.

15. The method of claim 1 wherein the spores used are of the species of the genus Bacillus.

16. The method of claim 15 wherein the spores used are selected from the group consisting of *Bacillus calidolactis*, *Bacillus subtilis*, *Bacillus stearothermophilus* and *Bacillus stearothermophilus* var. *calidolactis*.

17. The method of claim 16 wherein the spores used are *Bacillus stearothermophilus* var. *calidolactis* (L.M.D. 74.1).

18. The method of claim 1 wherein a mixture of spores of different organisms is used.

19. The method of claim 1 wherein the spore and agar mixture contains $10^5$ to $10^8$ spores of microorganisms per ml of agar medium.

20. The method of claim 1 wherein the spore and agar mixture contains $10^6$ to $10^7$ spores of microorganisms per ml of agar medium.

21. The method of claim 1 wherein the spores of a microorganism are obtained by cultivation of the microorganism in surface culture on agar or in a submerged liquid culture.

22. The method of claim 1 wherein the nutrients in the form of tablets are coated with a layer avoiding moisture transport from the medium into the tablets at ordinary or storage temperatures, but allowing nutrients to transport under the conditions.

23. The method of claim 22 wherein the coating layer consists of wax having a melting temperature of about 35° to 55°C.

24. The method of claim 16 wherein the incubation temperature is about 55° to 70°C.

25. The method of claim 16 wherein the incubation temperature is 60° to 65°C.

26. The method of claim 16 wherein the incubation period is about 1½ to 4 hours.

27. The method of claim 16 wherein the incubation period is 2 to 3 hours.

* * * * *